(12) United States Patent
Wyss et al.

(10) Patent No.: US 9,820,857 B2
(45) Date of Patent: Nov. 21, 2017

(54) SURGICAL INSTRUMENT AND METHOD OF USE

(71) Applicant: DEPUY IRELAND UNLIMITED COMPANY, County Cork OT (IE)

(72) Inventors: Joseph G. Wyss, Fort Wayne, IN (US); Terri L. Bong, West Bend, WI (US)

(73) Assignee: DEPUY IRELAND UNLIMITED COMPANY (IE)

( * ) Notice: Subject to any disclaimer, the term of this patent is extended or adjusted under 35 U.S.C. 154(b) by 1171 days.

(21) Appl. No.: 13/833,433

(22) Filed: Mar. 15, 2013

(65) Prior Publication Data

US 2014/0277541 A1   Sep. 18, 2014

(51) Int. Cl.
    A61B 17/88   (2006.01)
    A61F 2/38    (2006.01)
    A61F 2/46    (2006.01)

(52) U.S. Cl.
    CPC .............. *A61F 2/389* (2013.01); *A61F 2/46* (2013.01); *A61F 2/461* (2013.01)

(58) Field of Classification Search
    CPC ... A61F 2/461; A61B 17/92; A61B 2017/924; A61B 2017/925; A61B 2017/927; A61B 2017/928
    USPC .................................................. 606/99–100
    See application file for complete search history.

(56) References Cited

U.S. PATENT DOCUMENTS

| 6,520,966 B1 | 2/2003 | Kohler |
| 8,128,703 B2 | 3/2012 | Hazebrouck et al. |
| 8,277,460 B2 * | 10/2012 | McMillan .............. A61B 17/92 606/99 |
| 8,317,870 B2 | 11/2012 | Wagner et al. |
| 9,039,710 B2 * | 5/2015 | Blaylock .............. A61F 2/3859 269/254 CS |
| 2006/0200162 A1 * | 9/2006 | Farling ................ A61B 17/155 606/88 |
| 2008/0119941 A1 | 5/2008 | Seo |
| 2009/0036909 A1 * | 2/2009 | Perry ..................... A61F 2/461 606/157 |

(Continued)

FOREIGN PATENT DOCUMENTS

EP          0780090         6/1997

OTHER PUBLICATIONS

European Search Report, European Patent Application No. 14158769.1, dated May 23, 2014, 7 pages.

*Primary Examiner* — Matthew Lawson
(74) *Attorney, Agent, or Firm* — Barnes & Thornburg LLP

(57) ABSTRACT

A surgical instrument for use in an orthopaedic arthroplasty procedure includes a shaft having a first end and a second end and an impactor head disposed at the second end of the shaft. The impactor head includes first and second spaced ends, two spaced impaction surfaces disposed at the second end, and a cavity disposed between the impaction surfaces. The cavity is adapted to accommodate posterior-stabilizing spines of at least a first tibial implant component and a second tibial implant component having a size different than a size of the first tibial implant component. Each of the impaction surfaces includes a first section with a contour that conforms to a contour of a bearing surface of the first tibial implant component and a second section with a contour that conforms to a contour of a bearing surface of the second tibial implant component.

9 Claims, 21 Drawing Sheets

(56) References Cited

U.S. PATENT DOCUMENTS

| | | | |
|---|---|---|---|
| 2012/0123429 A1 | 5/2012 | Beedall et al. | |
| 2013/0006371 A1* | 1/2013 | Wogoman | A61F 2/4684 623/20.21 |
| 2013/0018382 A1* | 1/2013 | Jones | A61F 2/4603 606/99 |
| 2014/0094812 A1* | 4/2014 | Edwards | A61F 2/461 606/88 |
| 2014/0094821 A1* | 4/2014 | Wagner | A61F 2/461 606/99 |

* cited by examiner

SURGICAL INSTRUMENT AND METHOD OF USE

TECHNICAL FIELD

The present disclosure relates to surgical instruments and, more particularly, to methods and apparatuses for stabilizing surgical instruments during use.

BACKGROUND

Joint arthroplasty is a well-known surgical procedure by which a diseased and/or damaged natural joint is replaced by a prosthetic joint. A typical knee prosthesis includes a tibial component and a femoral component adapted to contact a bearing surface of the tibial component. The tibial component typically includes a stem extending distally therefrom that is implanted in a prepared medullary canal of the patient's tibia.

To facilitate the replacement of the natural joint with the knee prosthesis, orthopaedic surgeons use a variety of orthopaedic surgical instruments such as, for example, trial components, drill guides, reamers, impactors, and other surgical instruments.

SUMMARY

According to one aspect, a surgical instrument for use in an orthopaedic arthroplasty procedure includes a shaft having a first and second ends and an impactor head disposed at the second end of the shaft. The impactor head includes first and second spaced ends, two spaced impaction surfaces disposed at the second end of the impactor head, and a cavity disposed between the impaction surfaces. The cavity is adapted to accommodate posterior-stabilizing spines of at least a first tibial implant component and a second tibial implant component having a size different than a size of the first tibial implant component. In one embodiment, each of the impaction surfaces includes a first section with a contour that conforms to a contour of a bearing surface of the first tibial component and a second section with a contour that conforms to a contour of a bearing surface of the second tibial implant component.

The first section may include an anterior surface that contacts an anterior surface of the bearing surface of the first tibial implant component when the impactor head is positioned for impaction. The second section may include a posterior surface that contacts a posterior surface of the bearing surface of the second tibial implant component when the impactor is positioned for impaction.

In a further embodiment, the first section includes an inner surface that contacts an inner surface of the bearing surface of the first tibial implant component when the impactor head is positioned for impaction and the second section includes an outer surface that contacts an outer surface of the second tibial implant component when the impactor head is positioned for impaction.

In another embodiment, the size of the first tibial implant component is greater than the size of the second tibial implant component.

In a further embodiment, central surfaces of the impaction surfaces contact central surfaces of a third tibial implant component when the impactor head is positioned for impaction, wherein a size of the third tibial implant component is less than the size of the first tibial implant component and greater than the size of the second tibial implant component.

The surgical instrument may further include an anterior wall having an anterior wall extension that is adapted to contact an anterior portion of each of the first and second tibial implant components when in contact therewith.

The anterior wall extension may contact the posterior-stabilizing spine of the first tibial implant component when the impactor head is positioned for impaction and may contact a patellar bearing surface of the second tibial implant component when the impactor head is positioned for impaction.

In another aspect, a surgical instrument for use in an orthopaedic arthroplasty procedure includes a shaft having first and second ends and an impactor head attached to the second end of the shaft and including first and second spaced ends and two spaced impaction surfaces disposed at the second end of the impactor head. A cavity is disposed between the impaction surfaces and is adapted to accommodate posterior-stabilizing spines of a first tibial implant component and a second tibial implant component having a size different than a size of the first tibial implant component. An anterior wall is formed at the second end of the impactor head and includes an anterior wall extension that, in combination with the two spaced impaction surfaces, forms a stable surface for impacting at least the first and second tibial implant components. The anterior wall extension contacts the posterior-stabilizing spine of the first tibial implant component and a patellar bearing surface of the second tibial implant component when the impactor head is positioned for impaction on respective tibial components.

In an embodiment, the anterior wall extension and the impaction surfaces provide three stable points of contact for a plurality of different sizes of tibial implant components.

Each of the impaction surfaces may include a first section with a contour that conforms to a contour of a bearing surface of a first tibial implant component and a second section with a contour that conforms to a contour of bearing surfaces of the second tibial implant component.

The size of the first tibial implant component may be greater than the size of the second tibial implant component.

In another embodiment, the impaction surfaces contact bearing surfaces of the first tibial implant component such that anterior surfaces of the impaction surfaces contact anterior surfaces of the bearing surfaces and inner surfaces of the impaction surfaces contact inner surfaces of the bearing surfaces. The impaction surfaces may also contact bearing surfaces of the second tibial implant component such that posterior surfaces of the impaction surfaces contact posterior surfaces of the bearing surfaces and outer surfaces of the impaction surfaces contact outer surfaces of the bearing surfaces.

In a further aspect, a method of using a surgical instrument having a first and second ends, an impactor head disposed at the second end of the surgical instrument and including spaced apart impaction surfaces disposed at the first end of the impactor head, a cavity formed between the impaction surfaces, and an anterior surface extension extending from an anterior wall is disclosed. The method includes the steps of inserting a tibial implant component within a prepared tibia of the patient and positioning an end of the surgical instrument adjacent the tibial implant component with a posterior-stabilizing spine of the tibial implant component extending into the cavity of the impactor head. If a first tibial implant component having a first size is utilized, the method includes the step of positioning the anterior surface extension of the impactor head against an anterior camming surface of the posterior-stabilizing spine to provide stability to the impactor head during impaction of the tibial implant component. If a second tibial implant component having a second size different than the first size is utilized, the method includes the step of positioning the anterior surface extension of the impactor head against a patellar bearing surface of the second tibial implant component to provide stability to the impactor head during impaction of the tibial implant component.

The method may further include the step of positioning the impaction surfaces in contact with bearing surfaces of the first tibial implant component such that anterior surfaces of the impaction surfaces contact anterior surfaces of the bearing surfaces.

The method may also include the step of positioning the impaction surfaces in contact with the bearing surfaces of the first tibial implant component such that inner surfaces of the impaction surfaces contact inner surfaces of the bearing surfaces.

In an embodiment, the method further includes the step of positioning the impaction surfaces in contact with bearing surfaces of the second tibial implant component such that posterior surfaces of the impaction surfaces contact posterior surfaces of the bearing surfaces.

In another embodiment, the method includes the step of positioning the impactions surfaces in contacts with the bearing surfaces of the second tibial implant component such that outer surfaces of the impaction surfaces contact outer surfaces of the bearing surfaces.

Each of the impaction surfaces may have a first section with a contour that conforms to a contour of a bearing surfaces of the first tibial implant component and a second section with a contour that conforms to a contour of bearing surfaces of the second tibial component, wherein the size of the second tibial component is greater than the sizes of the first tibial component.

The anterior surface extension and the impaction surfaces may provide three stable points of contact for a plurality of different sizes of tibial implant components.

In another embodiment, the method includes the step of applying pressure to the first and second tibial implants, wherein a direction of the pressure is parallel to a longitudinal axis of the first and the second tibial implants.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which.

DETAILED DESCRIPTION OF THE DRAWINGS

Figure 1:
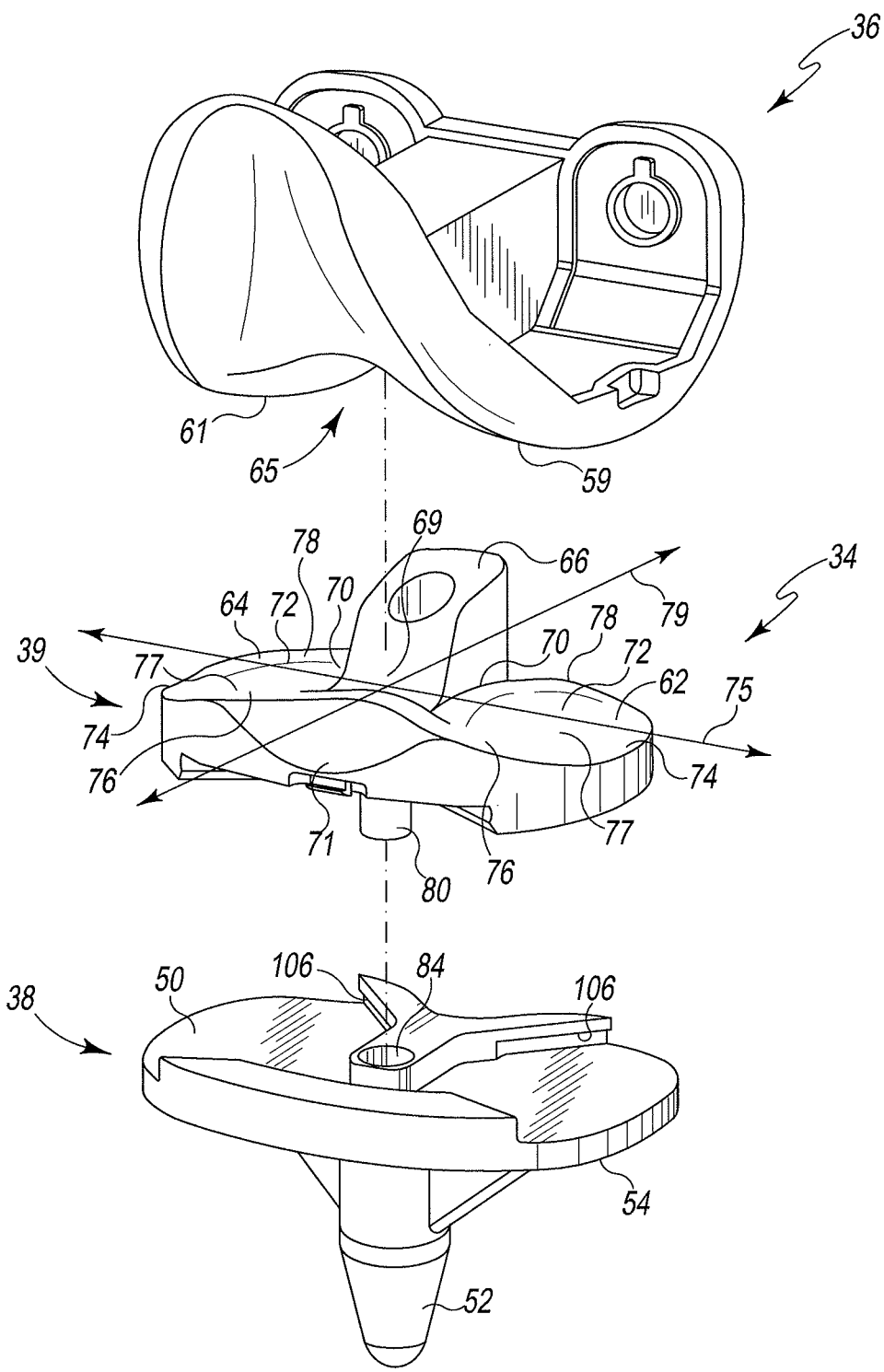
FIG. 1 is an exploded view of a knee prosthesis including a femoral component, a revision bearing, and a tibial tray.
Figure 2:
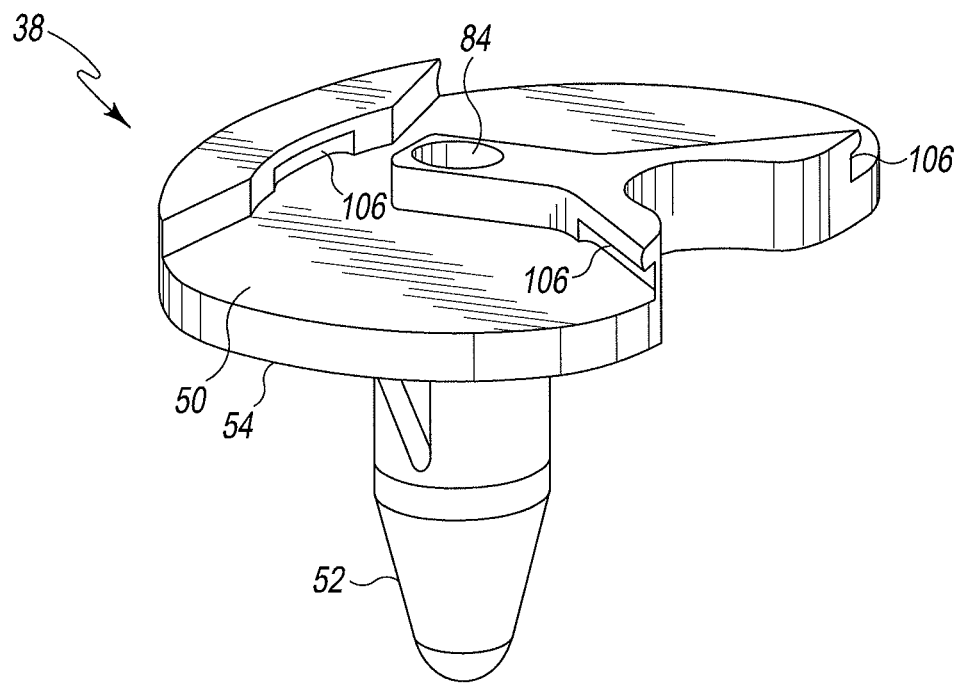
FIG. 2 is a top perspective view of a tibial tray of the knee prosthesis of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

A knee prosthesis 34 generally includes a femoral component 36, a tibial tray 38, and a bearing 39. An exemplary tibial tray 38 and bearing 39 are depicted in FIGS. 1-4. The tibial tray 38 includes a platform 50 having a fixation member, such as an elongated stem 52 extending away from its lower surface 54. The elongated stem 52 is configured to be implanted into a surgically prepared end of a patient's tibia. The bearing 39 is securable to the tibial tray 38. In particular, the bearing 39 may be snap-fit to the tibial tray 38, as discussed in detail in co-pending Wyss et al. U.S. application Ser. No. 13/788,921, entitled "Fixed-Bearing Knee Prosthesis Having Interchangeable Components," the disclosure of which is hereby incorporated by reference in its entirety.

Figure 4:
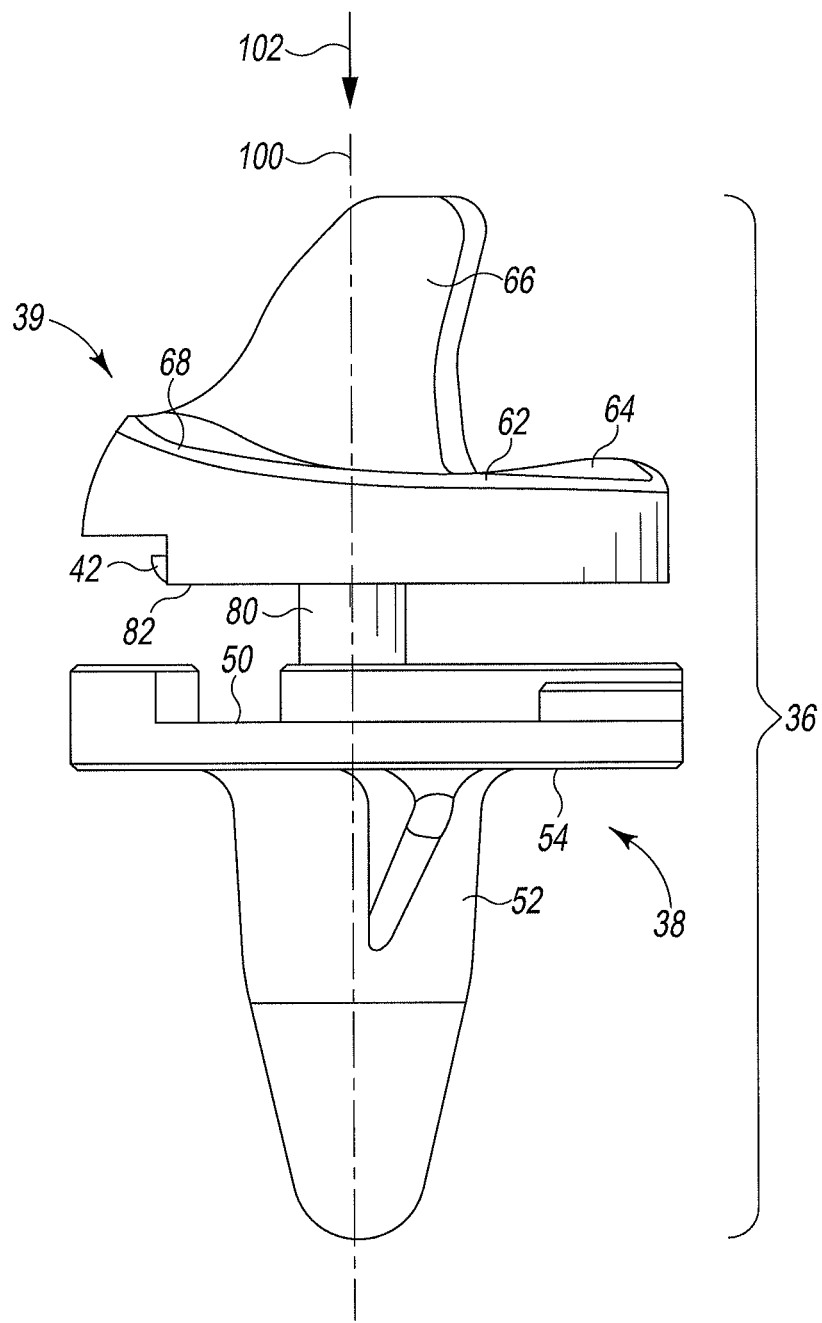
FIG. 4 is an exploded side elevational view showing a vertical installation of the revision bearing of FIG. 3 to the tibial tray of FIG. 2.

Referring to FIGS. 1 and 4, the bearing 39 includes bearing surfaces 62, 64 that are configured to articulate with a medial condyle surface 59 and a lateral condyle surface 61 of the femoral component 36. Specifically, the femoral component 36 is configured to be implanted into a surgically prepared end of the patient's femur, and is configured to emulate the configuration of the patient's natural femoral condyles. As such, the medial condyle surface 59 and the lateral condyle surface 61 are configured (e.g., curved) in a manner which mimics the condyles of the natural femur. The medial condyle surface 59 and the lateral condyle surface 61 are spaced apart from one another to define an intercondylar notch 65 therebetween.

The bearing 39 includes a posterior-stabilizing spine 66 extending upwardly from an upper surface 68 of the bearing 39 between the bearing surfaces 62, 64. Surfaces of the posterior-stabilizing spine 66 define an anterior camming surface 69 and a posterior camming surface (not shown) that engage corresponding cam surfaces defined in the femoral component to provide stability during flexion and extension of the knee prosthesis. A patellar surface 71 upon which the patella bears is disposed anterior of the anterior camming surface 69.

As seen in FIG. 1, each of the bearing surfaces 62, 64 includes an inner surface 70 adjacent the posterior-stabilizing spine 66, a central surface 72 forming the curved bearing surfaces, and an outer surface 74 opposite the inner surface, all of which are spaced along an axis 75. The bearing surfaces 62, 64 further include anterior surfaces 76, central surfaces 77, and posterior surfaces 78 spaced along an axis 79 parallel to the axis 75.

Figure 3:
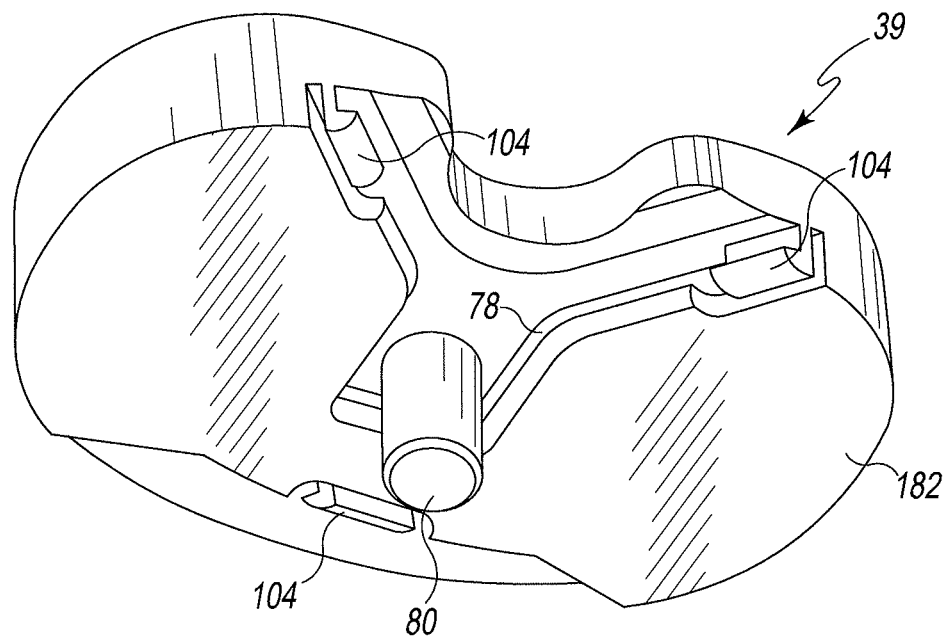
FIG. 3 is a bottom perspective view of the revision bearing of the knee prosthesis of FIG. 1.

Referring to FIGS. 3 and 4, the bearing 39 further includes a reinforcing pin 80 that extends downwardly from a lower surface 82 of the bearing 39. The reinforcing pin 80 may be of a solid construction or may have a bore (not shown) formed therein to accommodate a stiffening pin (not shown) that may be press fit or otherwise inserted into such a bore. As seen in FIG. 4, when the bearing 39 is installed within the tibial tray 38, the reinforcing pin 80 engages the tibial tray 38 first. In this manner, the reinforcing pin 80 is received into a bore 84 of the tibial tray 38, thereby requiring the bearing 39 and the reinforcing pin 80 to be vertically installed on the tibial tray 38. By vertically, it is meant that the bearing 39 is installed along a longitudinal axis 100 of the tibial tray 38 in the direction indicated by arrow 102. A number of flexible tabs 104 extending outwardly from the bearing 39 are configured to be retained within a number of undercuts 106 in the tibial tray 38 to secure the bearing 39 to the tibial tray 38. In order to position the tabs 104 within the undercuts 106, downwardly pressure in the direction 102 must be exerted on the bearing surfaces 62, 64.

The components of the knee prosthesis that engage the natural bone, such as the femoral component 36 and the tibial tray 38, may be constructed with biocompatible metal, such as a cobalt chrome alloy, although other materials may also be used. The bone engaging surfaces of these components may be textured to facilitate cementing the component to the bone. Such surfaces may also be porous coated to promote bone ingrowth for permanent fixation.

The bearing 39 may be constructed with a material that allows for smooth articulation between the bearing 39 and the femoral component, such as a polymeric material. One such polymeric material is ultra-high molecular weight polyethylene (UHMWPE)

As noted above, the construction of the tibial implant component requires the bearing 39 and the reinforcing pin 80 to be vertically installed on the tibial tray 38. A tool 130 for vertically driving the bearing 39 has therefore been designed for such installation and is depicted in FIGS. 5 and 6.

Figure 5:
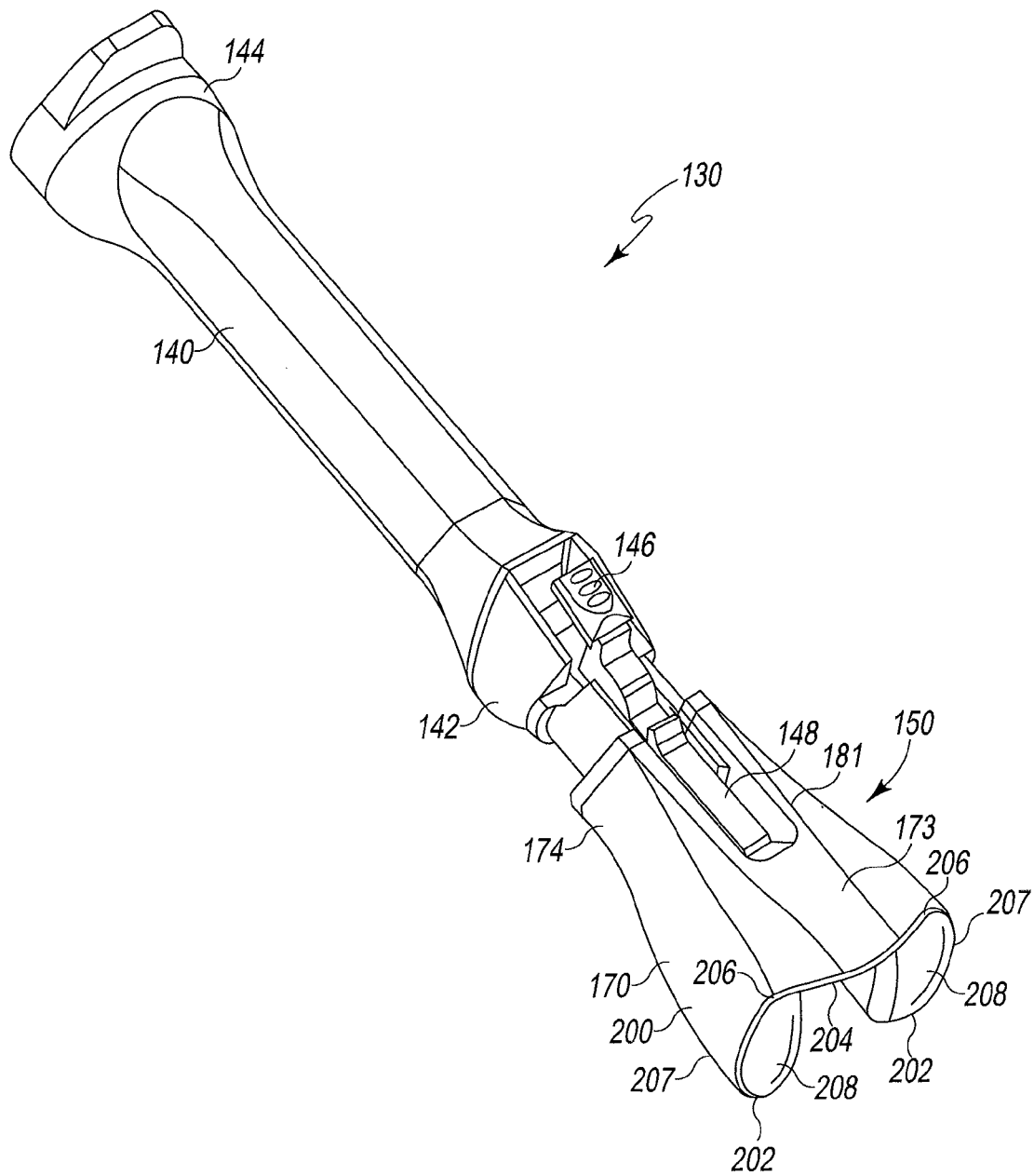
FIG. 5 is a perspective view of an impactor head attached to an end of a tool, wherein the impactor head is used to aid in driving the bearing of the knee prosthesis of FIG. 1 into securement with the tibial tray.
Figure 6:
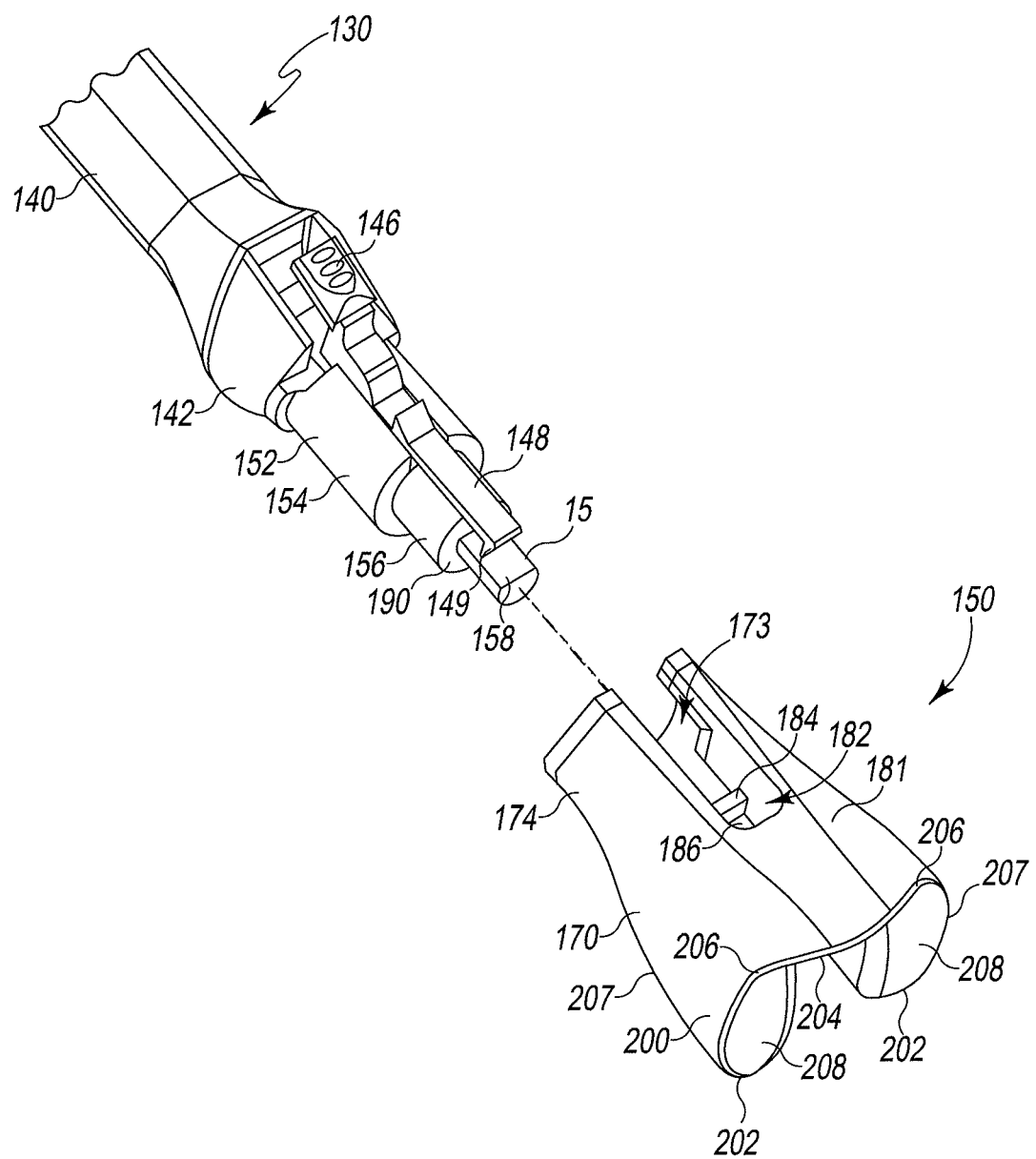
FIG. 6 is an exploded perspective view of the tool and the impactor head of FIG. 5.

As best seen in FIGS. 5 and 6, the tool 130 includes a central shaft 140 having an attachment end 142 and a free end 144. The attachment end 142 includes a universal quick-release connector having a lever arm 146 that operates a latch finger 148. A latch 149 is disposed at an end of the latch finger 148 to easily attach and detach various instrument end pieces to the tool 130, for example, an impactor head 150. The latch finger 148 is biased to a closed position such that inward movement of the lever arm 146 opens the latch finger 148. The attachment end 142 further includes a central projection 152 formed of a plurality of concentric cylinders 154, 156, 158 each extending from the next and each having a smaller diameter than the cylinder 154, 156, 158 from which it extends, with the cylinder 158 having a smallest diameter and the cylinder 154 having a largest diameter.

While the tool 130 is described herein as having an impactor head 150 attached thereto, any instrument end piece may be connected to the universal connector of the tool 130 including, but not limited to, punches, reamers, inserters, extractors, impactors, or any other instruments in which use of a hand piece or tool for controlling the instrument end piece is desired. During a particular surgery, the tool 130 may be utilized with a plurality of different end pieces to minimize the number of tools necessary in an operating room. Optionally, the tool 130 and impactor head 150 may be formed integrally.

The free end 144 of the tool 130 has a generally rounded form with a central, slightly raised circular portion (not shown) that provides a strike zone for receiving a blow from a tool, such as a hammer or mallet, during use of the tool 130. The central shaft 140 forms a handle by which the tool 130 may be grasped during use.

Figure 7:
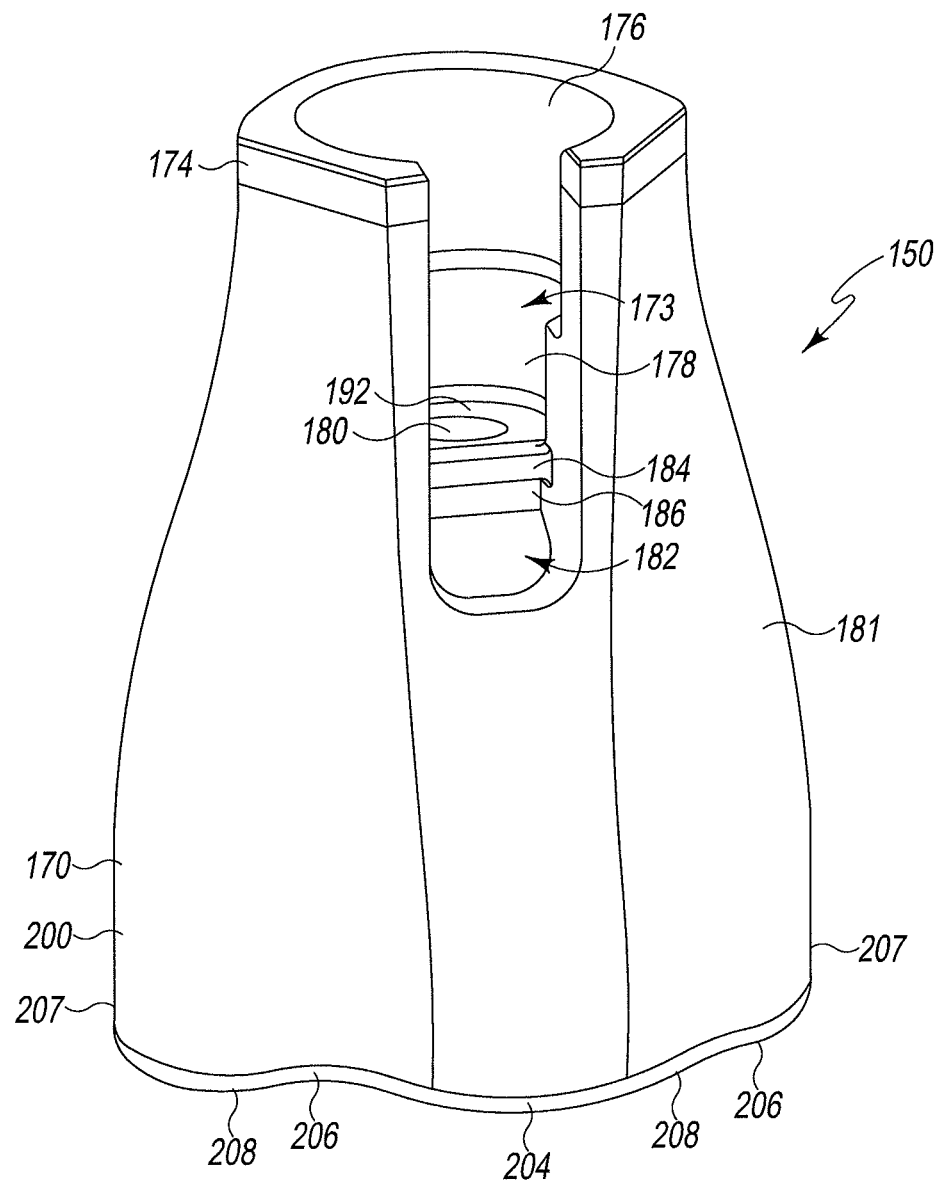
FIG. 7 is a perspective view of a top and an anterior side of the impactor head of FIGS. 5 and 6 and depicting a cutout formed in an end of the impactor head for attaching the impactor head to the tool.
Figure 8:
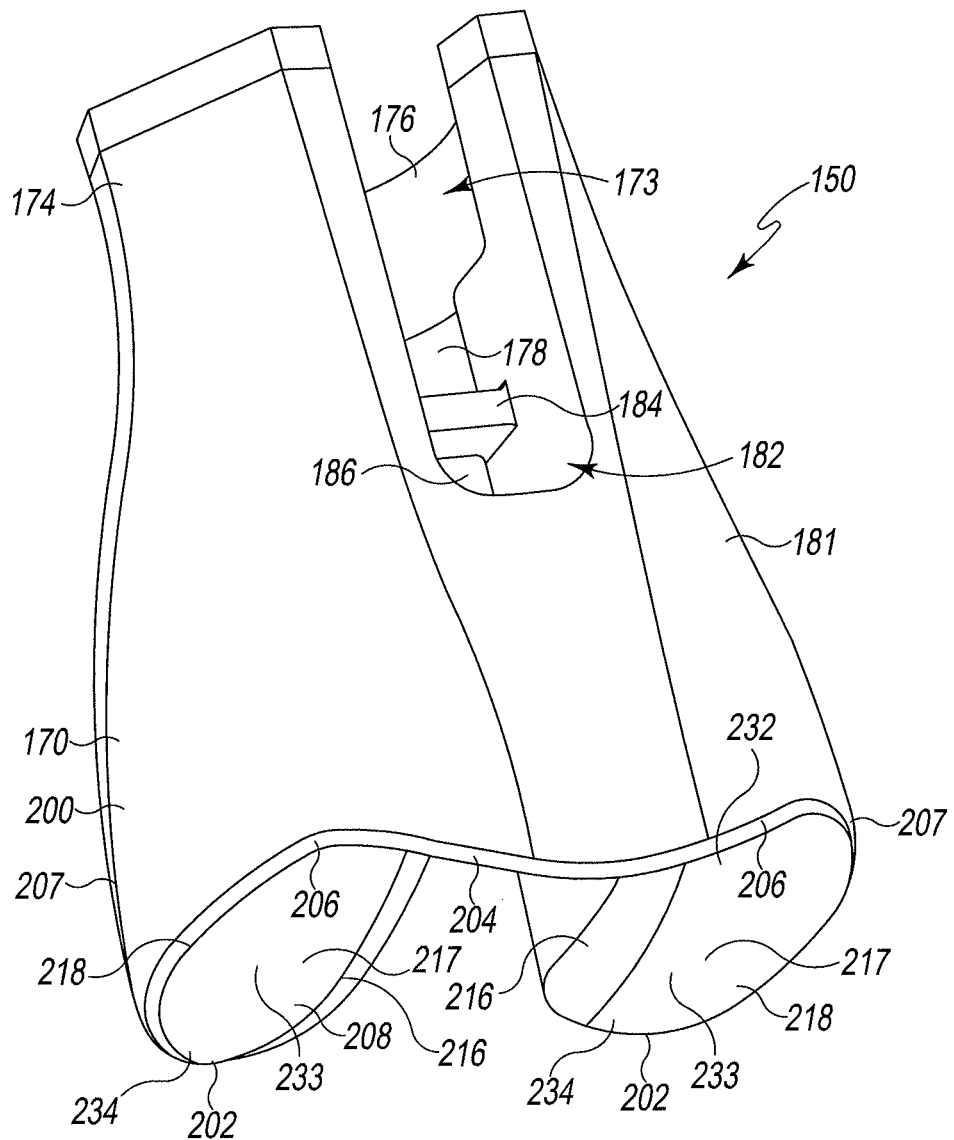
FIG. 8 is a perspective view of the anterior side and a bottom of the impactor head of FIGS. 5 and 6 and depicting an anterior surface extension extending outwardly from the impactor head.
Figure 9:
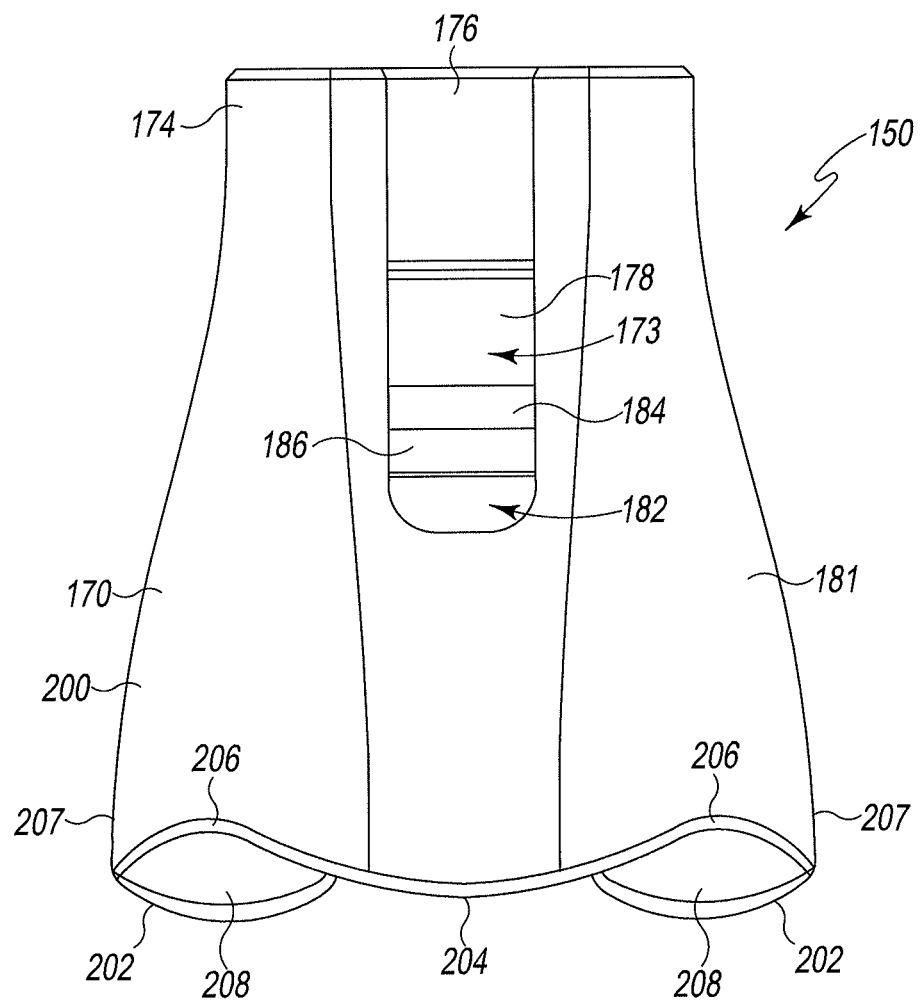
FIG. 9 is an elevational view of the anterior side of the impactor head of FIGS. 5 and 6.

Referring to FIGS. 7-9, the impactor head 150 includes a body 170 having a cavity 172 formed in an anterior surface 173 of an attachment end 174 of the impactor head 150. The cavity 172 includes cylindrical walls 176, 178, 180 that are concentrically disposed with respect to one another and stepped in diameter to form corresponding cylindrical cavities. In particular, the wall 176 has a diameter greater than diameters of the walls 178, 180 and the wall 178 has a diameter greater than the diameter of the wall 180. The walls 176, 178, 180 are sized to accommodate the cylinders 154, 156, 158, respectively, of the central projection 152 extending from the attachment end 142 of the tool 130, as will be discussed in greater detail below.

As seen in FIGS. 7-9, the impactor head 150 further includes an outer wall 181 having a cutout 182 formed therein, wherein the cutout 182 is in partial communication with the cavity 172 and extends below the cavity 172. A protrusion 184 extends outwardly from a surface 186 formed in the cutout 182 and is spaced inwardly of the outer wall 181.

The impactor head 150 is illustratively formed from a polymeric material such as ultra-high molecular weight polyethylene (UHMWPE), polyetheretherketone (PEEK), polyphenylsulfone (PPSU), polycarbonate (PC), but may be formed from other suitable materials.

The impactor head 150 is attached to the tool 130 by depressing the lever arm 146, thereby rotating the latch finger 148 about a hinge and lifting the latch finger 148. During this operation, the tool 130 is rotated until the latch finger 148 is aligned with the cutout 182 in the outer wall 181 of the impactor head 150 and the projection 152 of the tool 130 is inserted into the cavity 172 of the impactor head 150 with the cylinders 154, 156, 158 adjacent the walls 176, 178, 180, respectively. The projection 152 is inserted until an outer surface 190, as shown in FIG. 5, of the cylinder 156 is adjacent an inner surface 192, as shown in FIG. 6, forming a cylindrical cavity with the cylindrical wall 178. The lever arm 146 is thereafter released such that the latch finger 148 enters the cutout 182 and the latch 149 interferes with the protrusion 184 to prevent removal of the impactor head 150 from the tool 130. In a similar manner, the impactor head 150 may be removed by depressing the lever arm 146, thereby moving the latch finger 148 out of the cutout 182 and, thus, moving the latch 149 out of interference with the protrusion 184.

As discussed above, other instrument end pieces may be utilized with the tool 130. The other instrument end pieces may include structures similar to those of the impactor head 150, for example the cylindrical walls 176, 178, 180, the cutout 182, and the protrusion 184, to accommodate the attachment structures of the tool 130.

While the impactor head 150 is described as being attached to and detached from the tool 130 in a particular manner, it should be understood that the impactor head 150 may be attached to and/or detached from the tool 130 in any suitable manner.

Referring to FIGS. 7-12, the impactor head 150 includes an impact end 200 at an end of the body 170 opposite the attachment end 174. The impact end 200 of the impactor head 150 includes two spaced-apart impaction legs 202. As seen in FIGS. 3-5 and 8, an anterior surface extension 204 extends outwardly from the anterior surface 173 of the impactor head 150. The anterior surface extension 204 generally has a width that extends between centerpoints 206 of the impaction legs 202, but may alternatively extend any distance along the anterior surface 173. In one illustrative alternative embodiment, the anterior surface extension 204 extends between side edges 207 of the body 170 of the impactor head 150. Regardless, the width and the contour of the anterior surface extension 204 are intended to generally conform to a size and shape of the tibial bearing 39 with which the impactor head 150 is used, as will be discussed in greater detail below.

Figure 10:
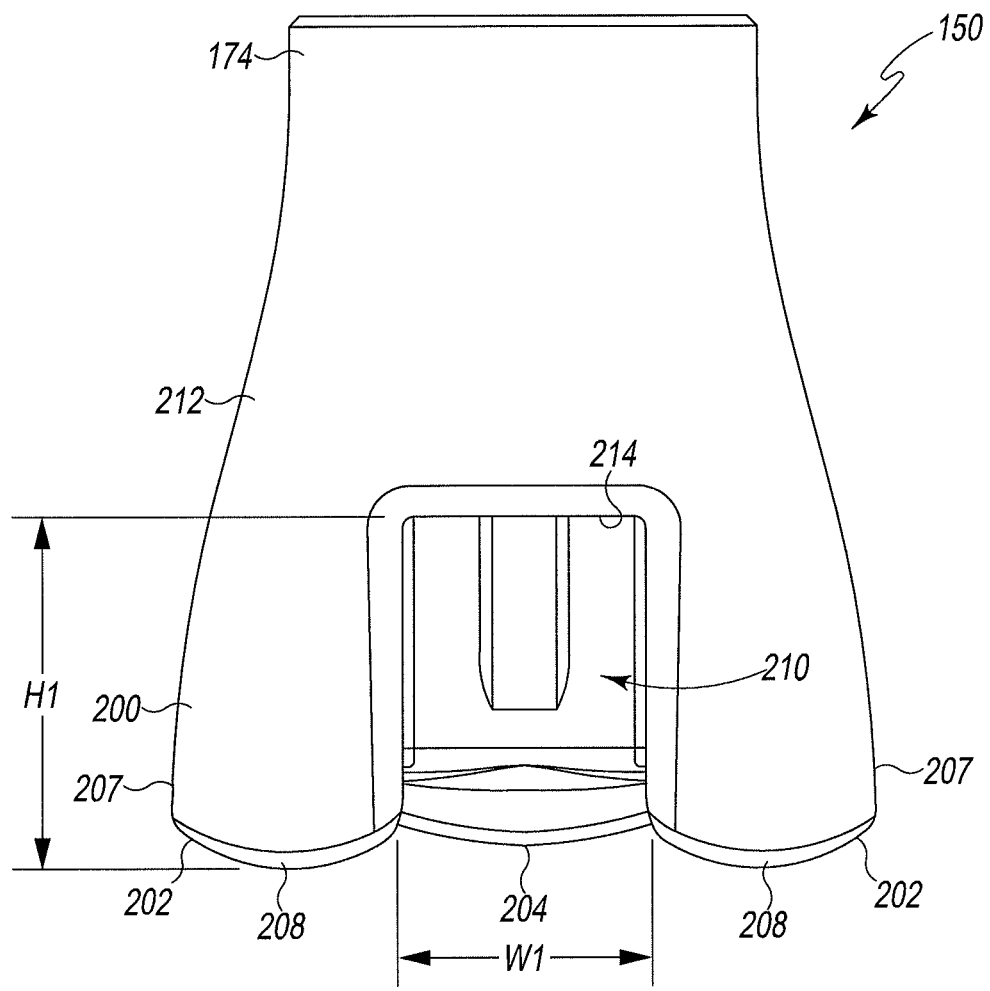
FIG. 10 is an elevational view of a posterior side of the impactor head of FIGS. 5 and 6 depicting a cavity formed between impaction legs of the impactor head.
Figure 11:
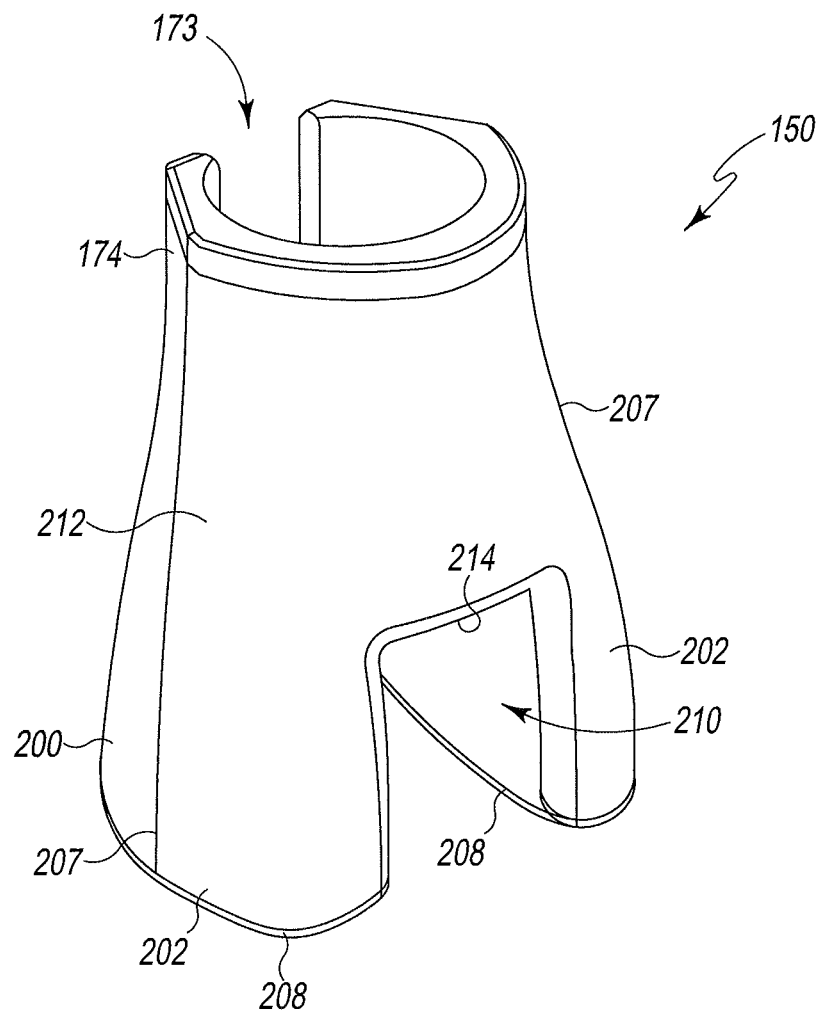
FIG. 11 is a perspective view of a top and the posterior side of the impactor head of FIGS. 5 and 6.
Figure 12:
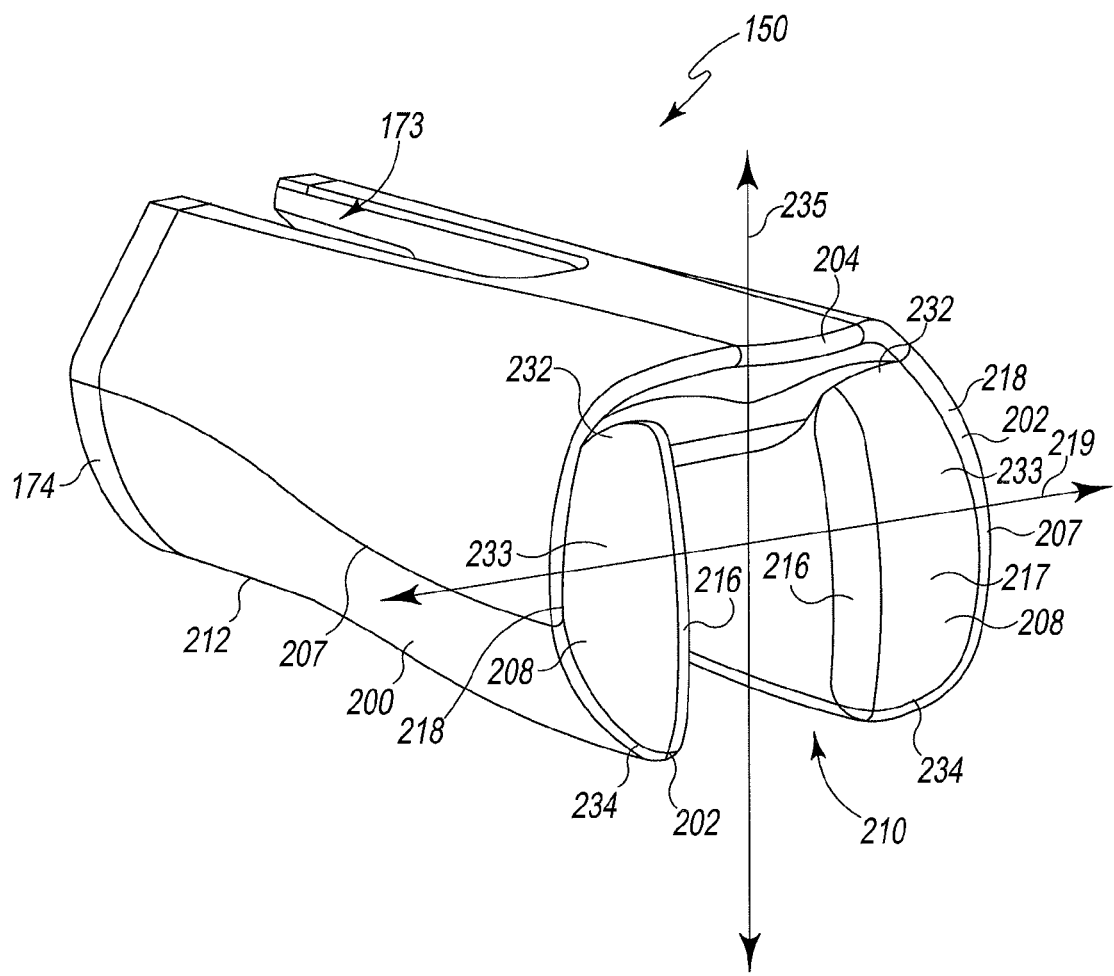
FIG. 12 is a perspective view of a side, the anterior side, and the bottom of the impactor head of FIGS. 5 and 6.

The impactor head 150 further includes a cavity 210 formed in a posterior surface 212 of the body 170 between the impaction legs 202, as shown in FIGS. 10-12. The cavity 210 has a width W1 extending laterally between the impaction legs 202 and a height H1 that extends longitudinally between impaction surfaces 208 and a wall 214 forming a top end of the cavity 210 and spaced between the impaction surfaces 208 and the cutout 182.

The impaction legs 202 terminate in forward impaction surfaces 208 that are adapted to conform to a shape of the bearing surfaces 62, 64 of the bearing 39, as will also be discussed in greater detail below. As best seen in FIGS. 8 and 10, each of the impaction surfaces 208 includes an inner surface 216 adjacent the cavity 210, a central surface 217, and an outer surface 218 opposite the inner surface 216, all of which are spaced along an axis 219, as seen in FIG. 12, that is parallel to the axis 75 when the impactor head 150 is in contact with the bearing 39. Each of the impaction surfaces 208 further includes an anterior surface 232, a central surface 233, and a posterior surface 234 that are spaced along an axis 235, which is parallel to the axis 79 when the impactor head 150 is positioned in contact with the bearing 39.

Various sizes of tibial implant components, including tibial trays 38 and bearings 39, may be provided (as well as femoral components 36). A single size of tibial tray 38 and a single size of bearing 39 compatible with the selected tibial tray 38 are selected for a patient. In an illustrative embodiment, the tibial trays 38 and the bearings 39 may be provided in sizes 1-10 with size 1 being the smallest and size 10 being the largest. As the size of the tibial trays 38 and the bearings 39 increases, so may the features of the tibial trays 38, and the bearings 39, for example, the bearing surfaces 62, 64 of the bearings 39.

Figure 13:
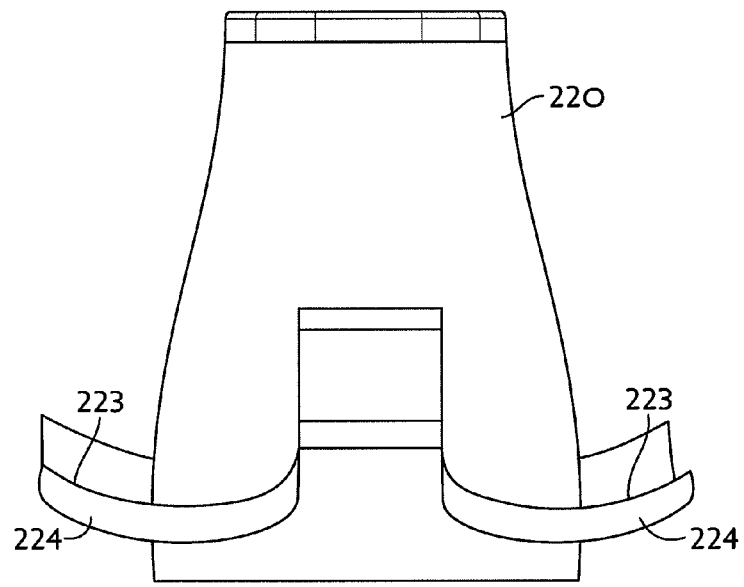
FIG. 13 is an elevational view of a posterior side of an impactor body prior to formation of impaction surfaces thereof.
Figure 14:
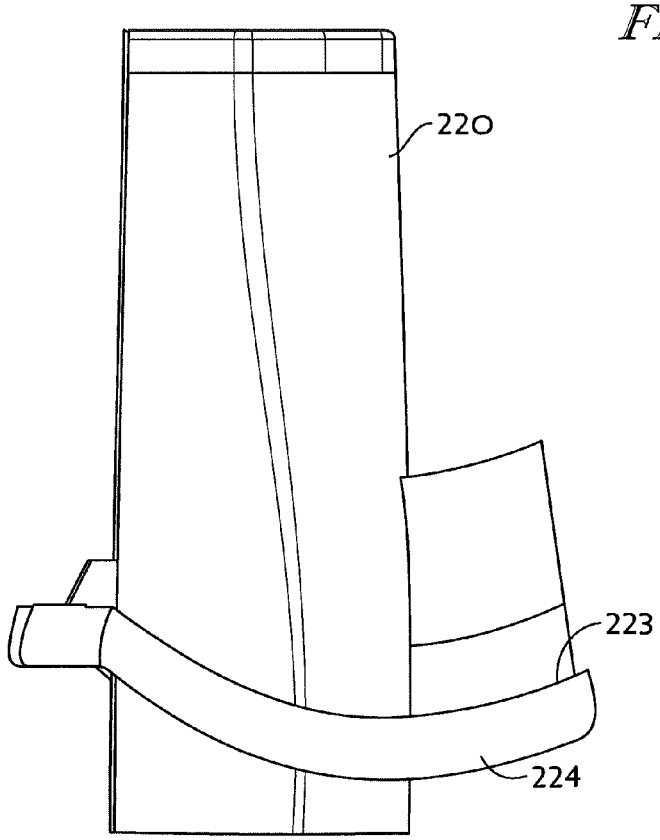
FIG. 14 is a side elevational view of the impactor body of FIG. 13 prior to formation of the impaction surfaces thereof.
Figure 15:
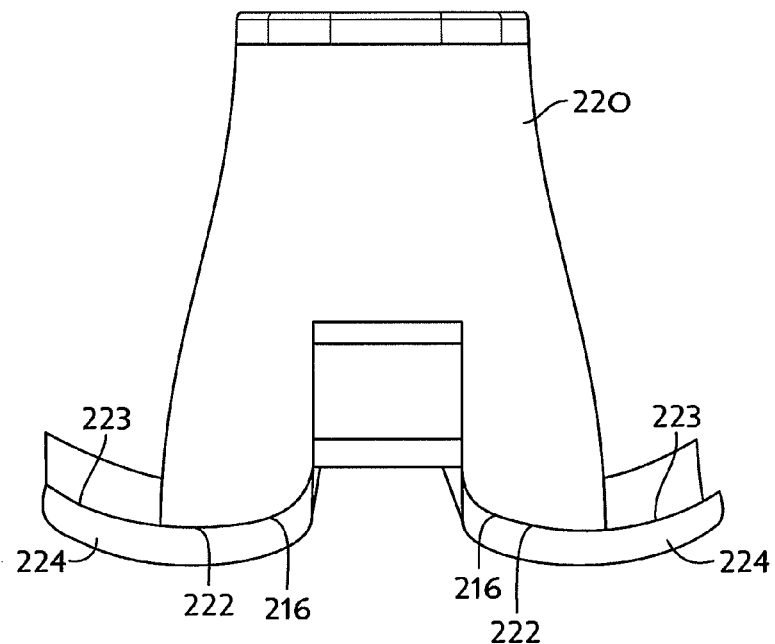
FIG. 15 is an elevational view of the posterior side of the impactor body after impaction surfaces have been partially formed using size 10 bearing surfaces.
Figure 16:
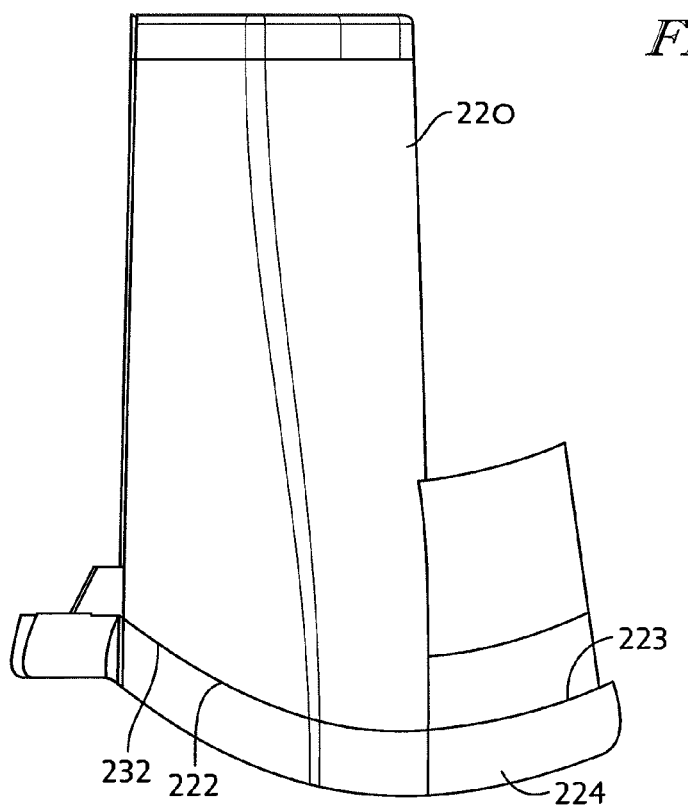
FIG. 16 is a side elevational view of the impactor body after impaction surfaces have been partially formed using the size 10 bearing surfaces.

Referring to FIGS. 13-21, the manner in which a contour of the forward impaction surfaces 208 of the impactor head 150 was shaped is depicted. In particular, various steps were undertaken to provide a contour or geometry to the impaction surfaces 208 that allows the impaction surfaces 208 to emulate the condyle surfaces 59, 61 and conform to the shape of the bearing surfaces 62, 64 of various bearings 39 (i.e., sizes 1-10). An image of an impactor body 220 is depicted in FIGS. 13 and 14 without formed impaction surfaces and depicting a geometry 223 of size 10 bearing surfaces 224 aligned therewith. The bearing surfaces 224 digitally emulate the size, shape, and contour of the tibial bearing 39. As seen in FIGS. 15 and 16, the size 10 bearing surfaces 224 are used to partially form the contour of the impaction surfaces 222, in particular, the inner surface 216 and the anterior surfaces 232 of the impaction surfaces 208.

Figure 17:
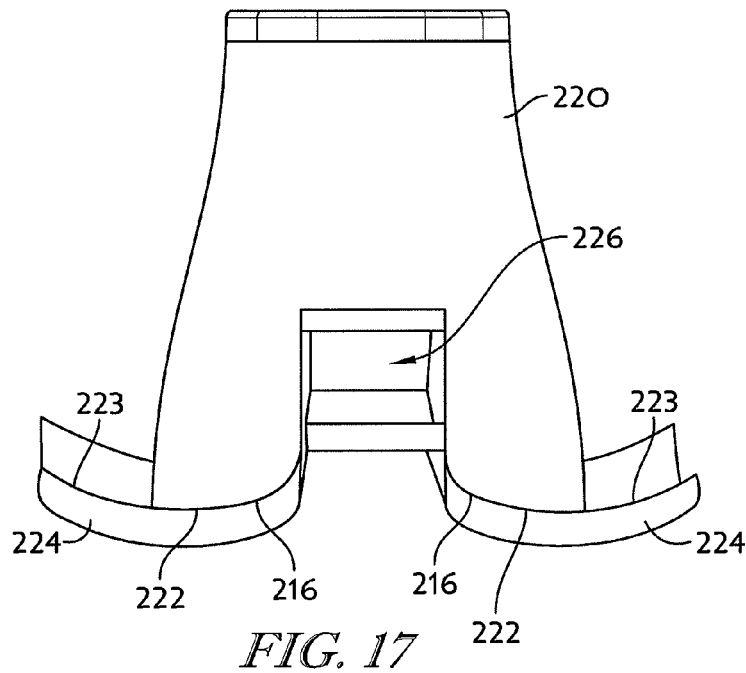
FIG. 17 is an elevational view of the posterior side of the impactor body after a through-hole has been formed in the impactor body for accommodating a spine of a size 10 tibial bearing.

The size 10 bearing surfaces 224 provide the partially formed impaction surfaces 222 with a geometry suitable for mating with at least the bearing surfaces of the size 10 insert tibial bearing. A through-hole 226 is thereafter formed through the impactor body 220, as seen in FIG. 17, such that the through-hole 226 will accommodate a size 10 spine. More specifically, the height H1 and the W1 of the finished cavity 210, as seen in FIG. 10, are large enough to accommodate the size 10 spine.

Figure 18:
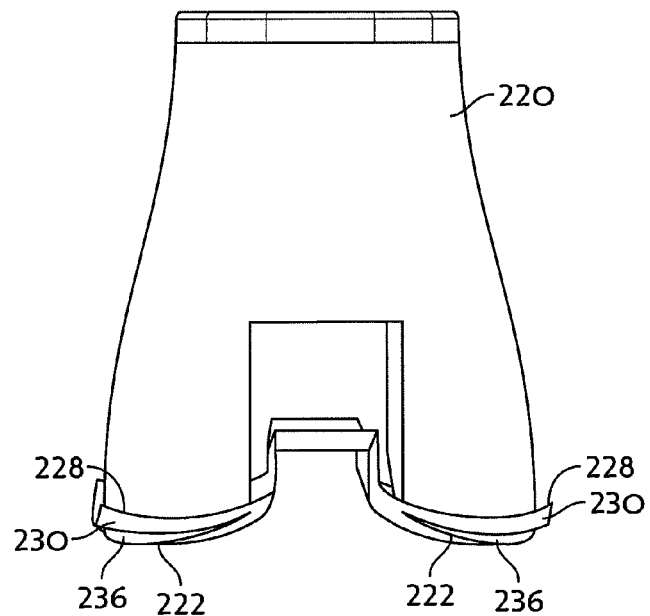
FIG. 18 is an elevational view of the posterior side of the impactor body depicting size 1 bearing surfaces and portions of the impactor body that are removed to form final impaction surfaces.
Figure 19:
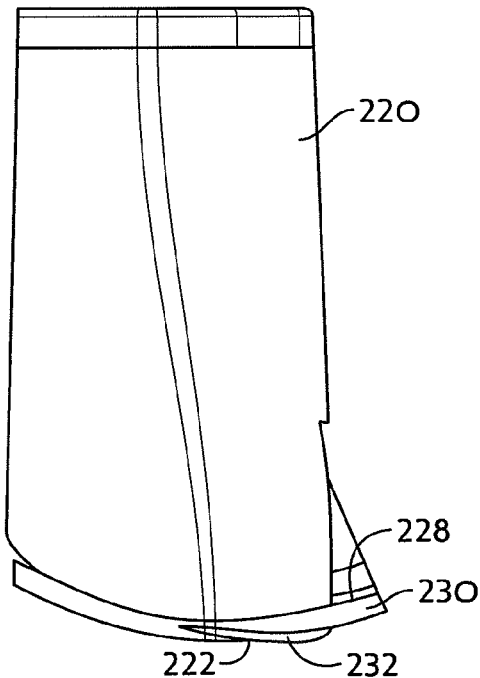
FIG. 19 is a side elevational view of the impactor body depicting the size 1 bearing surfaces and portions of the impactor body that are removed to form the final impaction surfaces.
Figure 20:
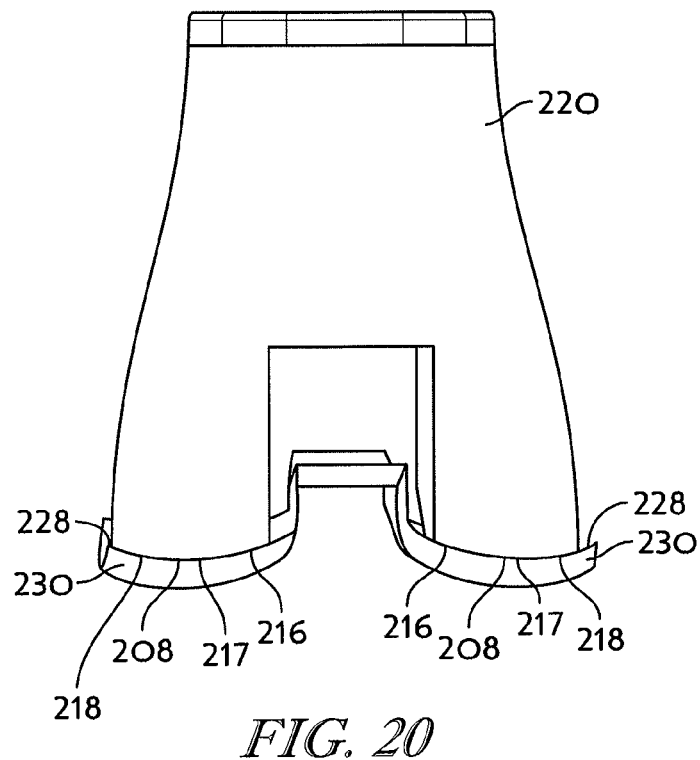
FIG. 20 is an elevational view of the posterior side of the impactor body, depicting the final impaction surfaces after material has been removed to conform to the size 1 bearing surfaces.
Figure 21:
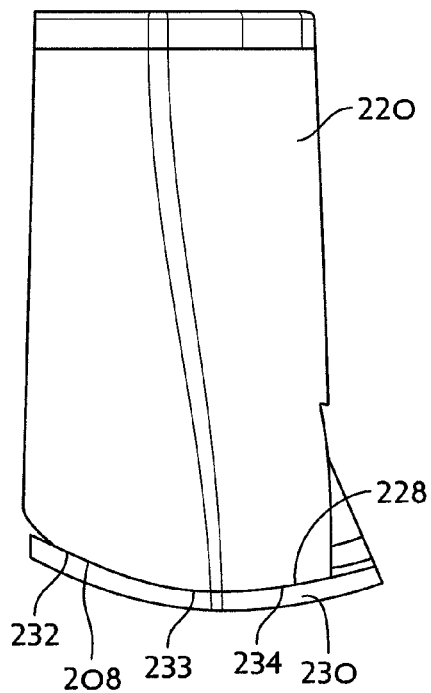
FIG. 21 is a side elevational view of the impactor body, depicting the final impaction surfaces after material has been removed to conform to the size 1 bearing surfaces.

A geometry 228 of size 1 bearing surfaces 230 is thereafter used to further form the impaction surfaces 222 of the impactor body 220. Specifically, the size 1 bearing surfaces 230 are depicted in FIGS. 18 and 19 intersecting the partially formed impaction surfaces 222 to indicate portions 236 of the impactor body 220 that are cut away or removed. The final impaction surfaces 208 are seen in FIGS. 20 and 21. The size 1 bearing surfaces 230 provide the final impaction surfaces 208 with a geometry suitable for mating with bearing surfaces of the size 1 insert tibial bearing. More specifically, the outer surfaces 218 and the posterior surfaces 234 of the impaction surfaces 208 conform to at least the size 1 bearing. Since the size 10 and size 1 bearing surfaces 224, 230 are used to form the final impaction surfaces 208, the final impaction surfaces 208 conform to all sizes of tibial bearings, for example, tibial bearing sizes 1 through 10.

While the principles of the present disclosure are described for use with tibial bearings having sizes 1 through 10, it should be understood that the principles discloses herein may be used with any number of differently-sized tibial implant components. Also, while the shaping or forming steps described herein are described with respect to a smallest tibial bearing and a largest tibial bearing, the shaping or forming steps may be accomplished with any sizes of tibial bearings.

Figure 22:
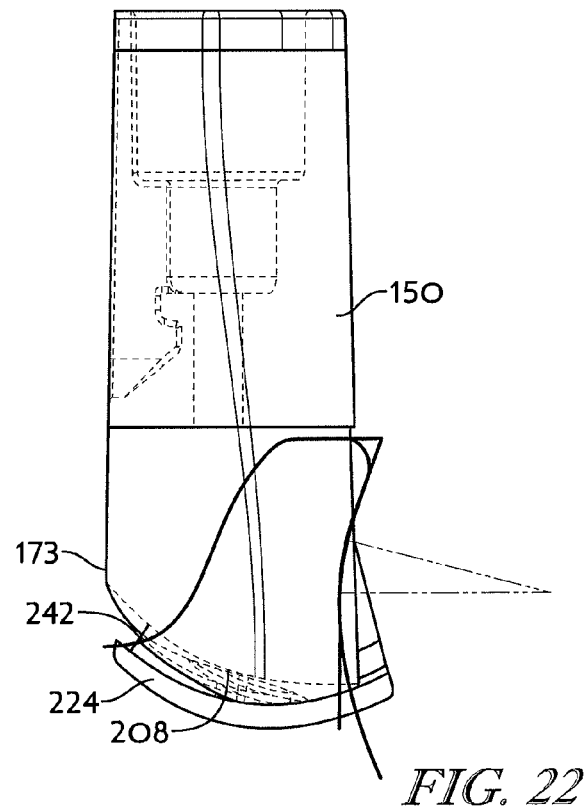
FIG. 22 is a side elevational view of the impactor body with the final impaction surfaces disposed adjacent bearing surfaces of the size 10 bearing surfaces and depicting an end of the impactor body as transparent in order to view a spine of the size 10 bearing.
Figure 23:
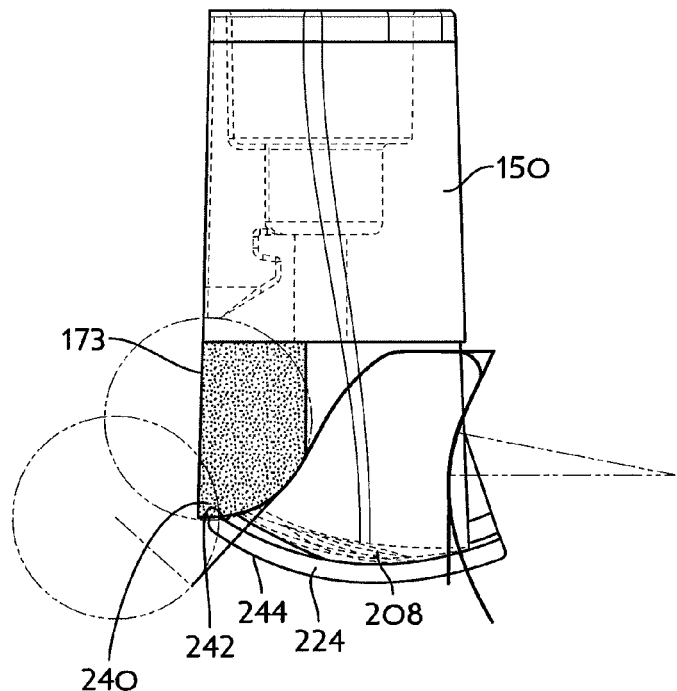
FIG. 23 is a side elevational view similar to the view of FIG. 22 and depicting an extrusion extending from an anterior wall of the impactor head, wherein the extrusion conforms to a shape of an anterior camming surface of the size 10 bearing surfaces.
Figure 24:
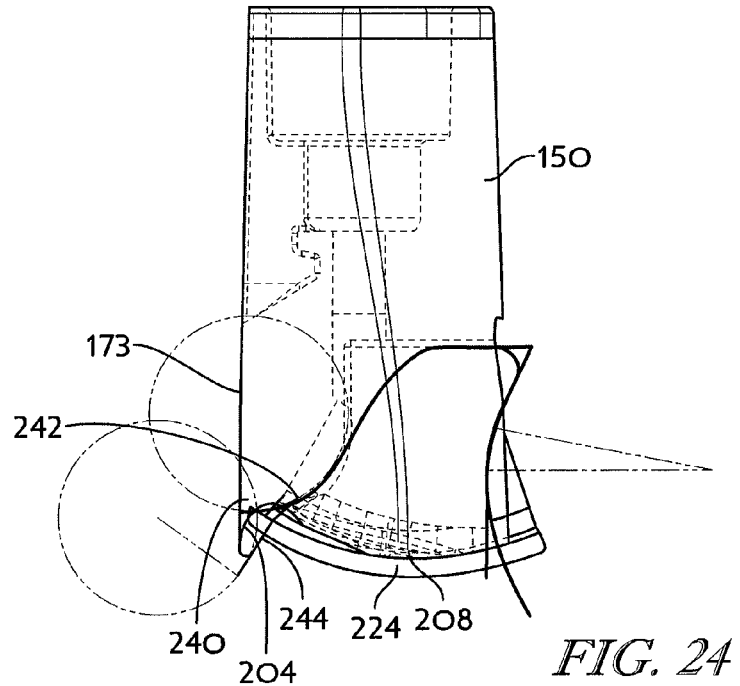
FIG. 24 is a side elevational view similar to the view of FIG. 23 and further depicting the anterior surface extension after full formation thereof.

Referring now to FIGS. 22-24, the steps undertaken to form a contour of the anterior surface extension 204 of the impactor head 150 are depicted. The impactor head 150 is depicted in FIG. 22 with the impaction surfaces 208, after formation thereof, in contact with bearing surfaces of the size 10 bearing surfaces 224, prior to formation of the anterior surface extension 204. Referring to FIG. 23, an extrusion 240 is formed extending from the anterior wall 173 of the impactor head 150 and conforming to an anterior camming surface 242 of the size 10 bearing surfaces 224. As also seen in FIG. 23, the extrusion 240 has a geometry that also conforms to a patellar curve 244. Using the patellar curve 244, the anterior wall 173 is formed, as seen in FIG. 24.

Although specific steps during the surgical procedure will be described in detail, one skilled in the art will appreciate that the present application is not limited to these specific steps and the tool 130 with the impactor head 150 attached may be used in any sequence of steps as preferred by a particular surgeon and depending on the steps necessary during the surgical procedure.

Use of the tool 130 with the attached impactor head 150 during a total knee replacement surgical procedure will now be briefly discussed with reference to FIGS. 25-28. In a revision surgical procedure, the tibial tray 38 would already be implanted within the patient's resected tibia. The primary bearing (not shown) would be removed using a suitable instrument and an appropriately sized revision bearing 39 would be selected. While a revision surgical procedure is described, it should be understood that the surgical procedure may include the steps of resecting, reaming, and/or preparing the tibia, drilling the proper holes in the patient's tibial bone surface, and installing the tibial tray 38.

As depicted in and described with respect to FIG. 4, the reinforcing pin 80 of the bearing 39 is inserted into the bore 84 of the tibial tray 38 and the bearing 39 is moved downwardly until the tabs 90 of the bearing 39 reach the undercuts 92 of the tibial tray 38. The tool 130 is thereafter positioned with the impaction surfaces 208 of the impactor head 150 adjacent the bearing surfaces 62, 64 of the bearing 39. In this position, the posterior-stabilizing spine 66 of the bearing 39 is positioned within the cavity 172 formed within the impactor head 150

Figure 25:
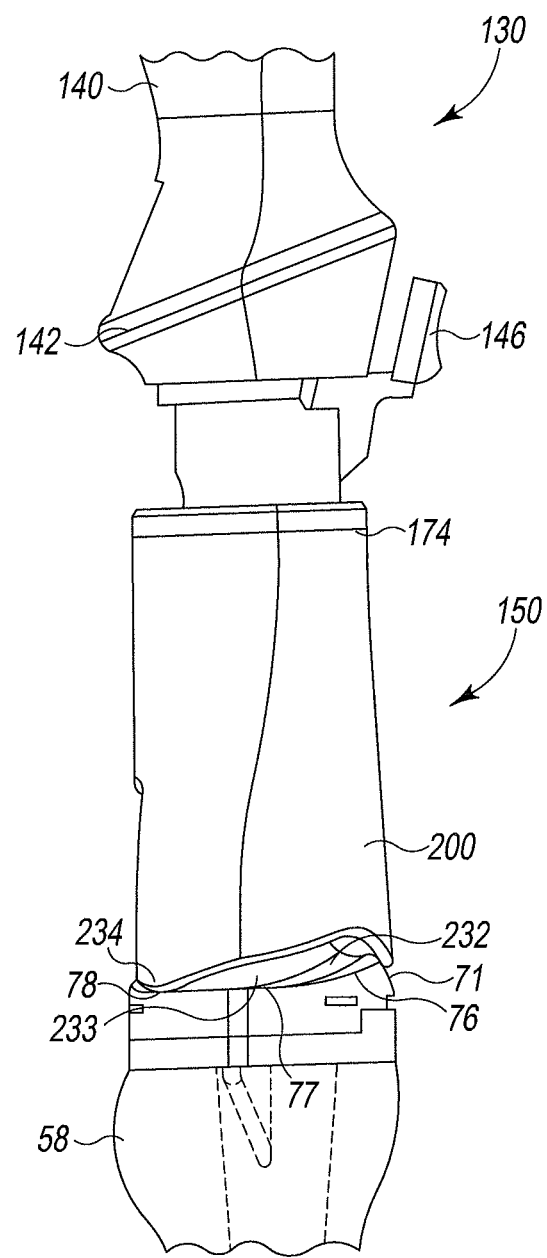
FIG. 25 is a side elevational view of the tool and impactor of FIGS. 5 and 6 with the impactor in contact with a size 1 revision bearing.
Figure 26:
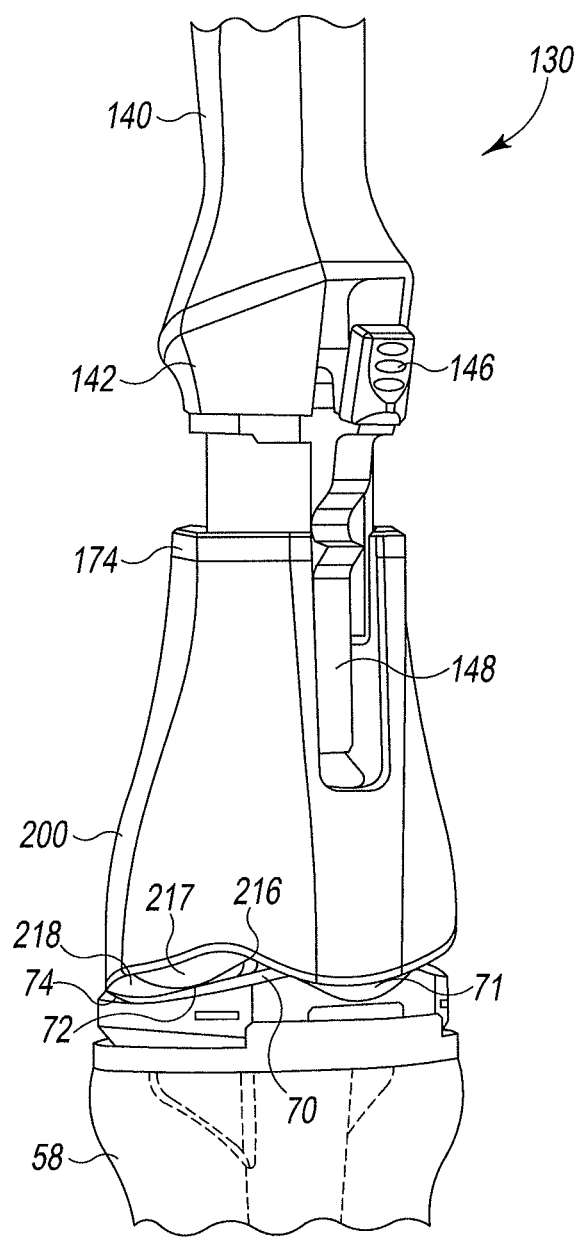
FIG. 26 is a perspective view of the tool and impactor of FIGS. 5 and 6 with the impactor in contact with the size 1 revision bearing.
Figure 27:
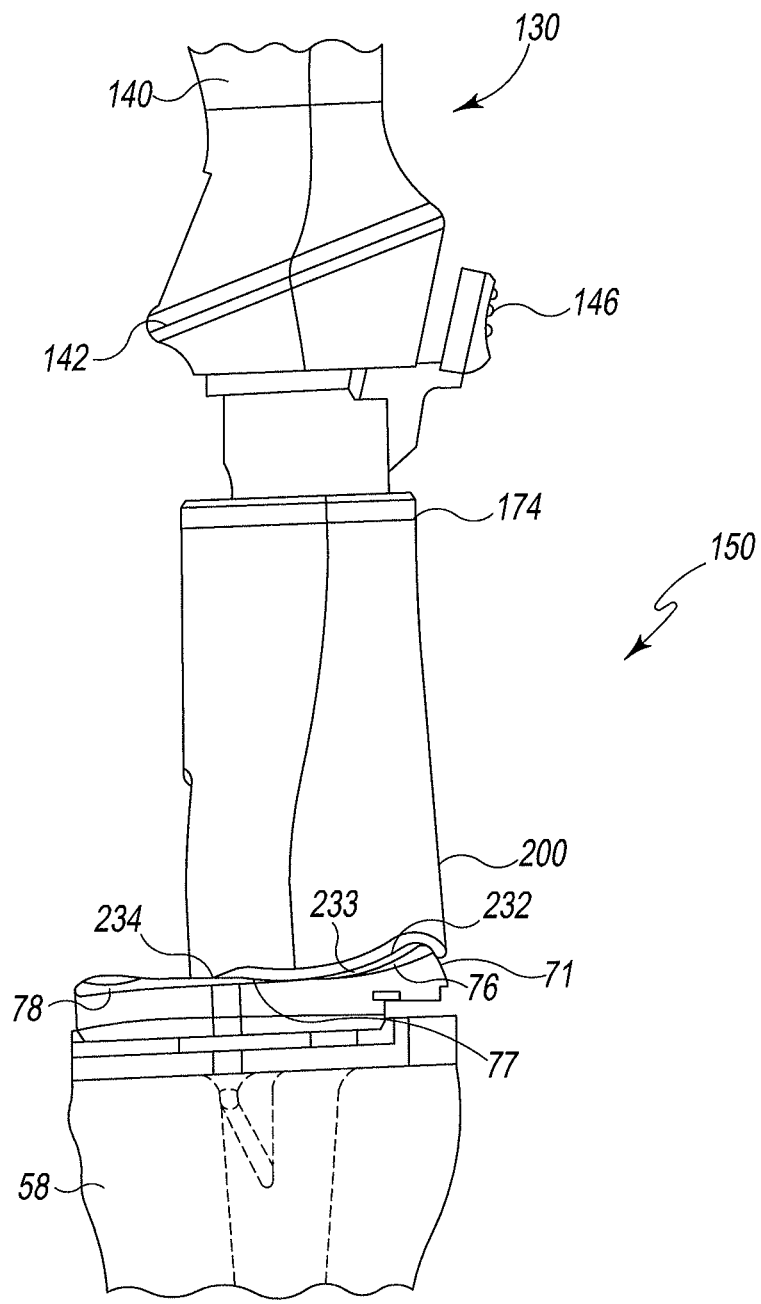
FIG. 27 is a side elevational view of the tool and impactor of FIGS. 5 and 6 with the impactor in contact with a size 10 revision bearing.
Figure 28:
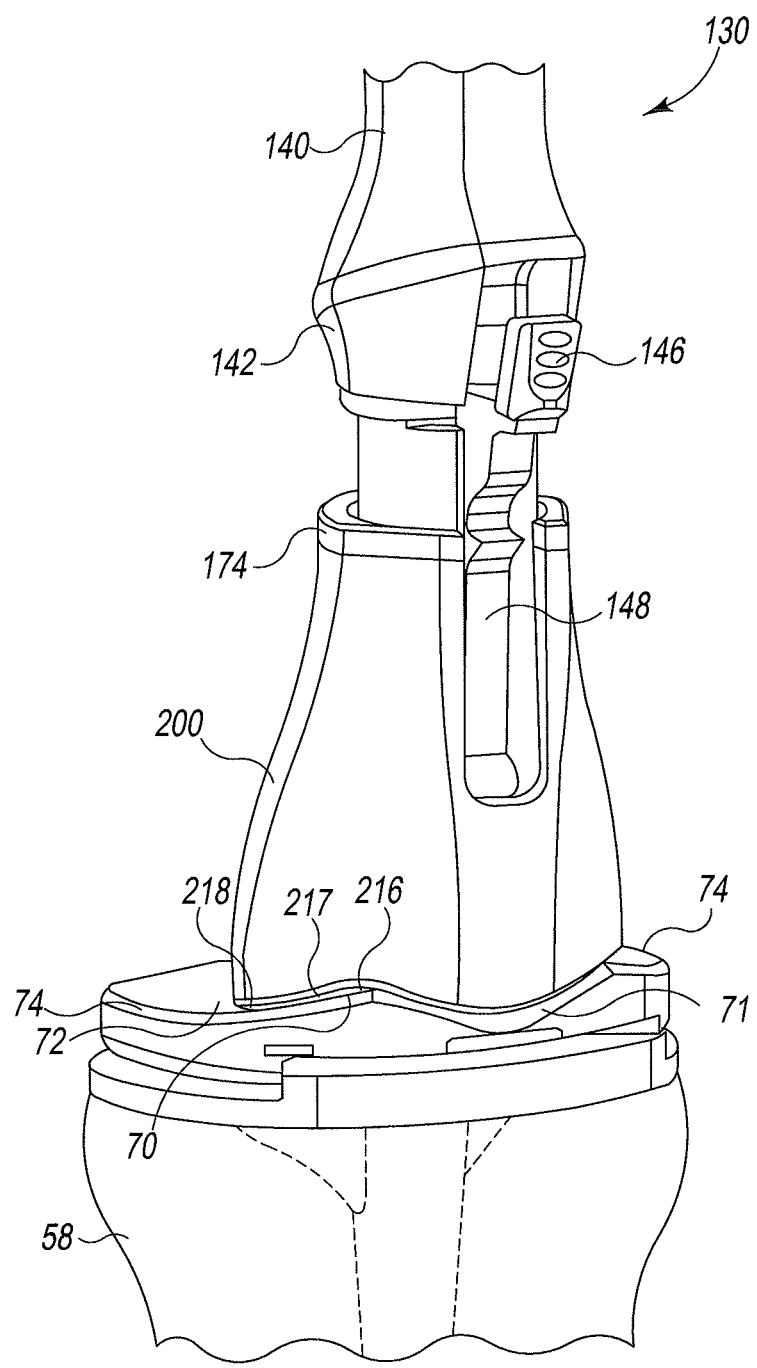
FIG. 28 is a perspective view of the tool and impactor of FIGS. 5 and 6 with the impactor in contact with the size 10 revision bearing.

As described in detail above, the impaction surfaces 208 and the anterior surface extension 204 are formed with contours that prevent rocking of the impactor head 150 regardless of a size of the bearing 39. In particular, the impaction surfaces 208 and the anterior surface extension 204 provide three points of direct and stable contact for each bearing 39. For example, when used with smaller bearings 39, for example a size 1 bearing, outer surfaces 218 of the impaction surfaces 208 contact outer surfaces 74 of the bearing surfaces 62, 64, posterior surfaces 234 of the impaction surfaces 208 contact posterior surfaces 78 of the bearing surfaces 62, 64, and the anterior surface extension 204 contact the patellar surface 71 of the bearing 39, as seen in FIGS. 25 and 26. When used with larger bearings 39, for example a size 10 bearing, inner surfaces 216 of the impaction surfaces 208 contact inner surfaces 70 of the bearing surfaces 62, 64 of the larger bearings 39, anterior surfaces 232 of the impaction surfaces 208 contact anterior surfaces 76 of the bearing surfaces 62, 64, and the anterior surface extension 204 contacts the anterior camming surface 69 of the spine 66 of the bearing 39, as seen in FIGS. 27 and 28. When used with a medium-sized bearing 39, for example a size 5 bearing, central surfaces 217 of the impaction surfaces 208 may contact central surfaces 72 of the bearing surfaces 62, 64 and the anterior surface extension 204 may contact a point between the anterior camming surface 69 of the spine 66 and the patellar surface 71 of the bearing 39. Regardless of the size of bearing 39, the impaction surfaces 208 and the anterior surface extension 204 provide three surfaces that conform to three different contact points on each bearing 39 to provide a stable impaction surface.

After the impactor head 150 is positioned appropriately against the bearing 39, the bearing 39 is forced against the tibial tray 38 by using a hammer, mallet, or other suitable tool to strike the free end 144 of the tool 130. Pressure is exerted in the direction 102 by striking the free end 144 of the tool 130 forces the tabs 90 on the bearing 39 past the undercuts 92 in the tibial tray 38 and securing the bearing 39 on the tibial tray 38. A surgeon may need to strike the free end 144 of the tool 130 multiple times to appropriately seat the bearing 39.

While particular tibial implant components are depicted herein, the principles of the present application may be used with other tibial components. Further, the tool 130 may be used in conjunction with various other instrument end pieces during the surgical process.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A system for use in an orthopaedic arthroplasty procedure, the system comprising:
 a first tibial implant component having a first size and including a first bearing surface and a first posterior-stabilizing spine, the first bearing surface including a first concave contour,
 a second tibial implant component having a second size different from the first size and including a second bearing surface and a second posterior-stabilizing spine, the second bearing surface including a second concave contour, and
 a surgical instrument comprising:
 (i) a shaft having a first end and a second end;
 (ii) an impactor head disposed at the second end of the shaft and including:
  first and second spaced ends;
  two spaced legs disposed at the second end of the impactor head, each leg having a first surface; and
  a cavity disposed between the first surfaces of the spaced legs, wherein the cavity is adapted to accommodate the first and second posterior-stabilizing spines of the first tibial implant component and the second tibial implant component;
 wherein each leg also includes a second surface and an arced third surface that connects the first surface and the second surface,
 wherein each of the second surfaces includes a first section with a first convex contour configured to engage and conform to the first concave contour of the first bearing surface of the first tibial implant component and a second section with a second convex contour configured to engage and conform to the second concave contour of the second bearing surface of the second tibial implant component.

2. The system of claim 1, wherein:
 the first section includes an anterior surface that contacts an anterior surface of the first bearing surface of the first tibial implant component when the impactor head is positioned for impaction; and
 the second section includes a posterior surface that contacts a posterior surface of the second tibial implant component when the impactor head is positioned for impaction.

3. The system of claim 1, wherein:
 the first section includes an inner surface that contacts an inner surface of the first bearing surface of the first tibial implant component when the impactor head is positioned for impaction; and
 the second section includes an outer surface that contacts an outer surface of the second tibial implant component when the impactor head is positioned for impaction.

4. The system of claim 3, wherein the first size of the first tibial implant component is greater than the second size of the second tibial implant component.

5. The system of claim 3, further comprising:
 a third tibial implant component having a plurality of central surfaces and a third size,
 wherein the second surface of each leg includes a central surface that is configured to contact the central surfaces of the third tibial implant component when the impactor head is positioned for impaction and wherein the third size of the third tibial implant component is less than the first size of the first tibial implant component and greater than the second size of the second tibial implant component.

6. The system of claim 1, further including an anterior wall that extends away from the legs and is adapted to contact an anterior portion of each of the first and second tibial implant components when in contact therewith.

7. The system of claim 6, wherein:
 the anterior wall contacts the posterior-stabilizing spine of the first tibial implant component when the impactor head is positioned for impaction; and
 the anterior wall contacts a patellar bearing surface of the second tibial implant component when the impactor head is positioned for impaction.

8. A system for use in an orthopaedic arthroplasty procedure, the system comprising:
 a first tibial implant component having a first size and including a first bearing surface and a first posterior-stabilizing spine, the first bearing surface including a first concave contour,
 a second tibial implant component having a second size different from the first size and including a second bearing surface and a second posterior-stabilizing spine, the second bearing surface including a second concave contour, and
 an impactor head comprising:
 a body that has first and second spaced ends;
 two spaced legs disposed at the second end of the body, each leg having a first surface;
 a cavity disposed between the first surfaces of the spaced legs, wherein the cavity is adapted to accommodate posterior-stabilizing spines of the first tibial implant component and the second tibial implant component; and
 an anterior wall extending away from the legs at the second end of the body, the anterior wall, in combination with the two spaced legs, forms a stable surface for impacting at least the first and second tibial implant components;
 wherein the anterior wall contacts the posterior-stabilizing spine of the first tibial implant component when the impactor head is positioned for impaction and the anterior wall contacts a patellar bearing surface of the second tibial implant component when the impactor head is positioned for impaction.

9. The system of claim 8, wherein the first size of the first tibial implant component is greater than the second size of the second tibial implant component.

* * * * *